United States Patent [19]

Matsushita et al.

[11] Patent Number: 4,726,930

[45] Date of Patent: Feb. 23, 1988

[54] APPARATUS FOR CHROMATOGRAPHIC ANALYSIS

[75] Inventors: Susumu Matsushita; Tetsuo Ikushige, both of Yamaguchi, Japan

[73] Assignee: Toyo Soda Manufacturing Co., Ltd., Yamaguchi, Japan

[21] Appl. No.: 769,921

[22] Filed: Aug. 27, 1985

Related U.S. Application Data

[62] Division of Ser. No. 656,212, Oct. 1, 1984.

[30] Foreign Application Priority Data

Oct. 1, 1983 [JP] Japan ................ 58-181823
Oct. 1, 1983 [JP] Japan ................ 58-183730

[51] Int. Cl.$^4$ .............. G01N 30/02; G01N 30/96
[52] U.S. Cl. .................. 422/70; 73/61.1 C; 210/198.2; 210/321.1; 210/649; 210/656; 210/321.72; 436/161; 436/175; 436/178
[58] Field of Search .............. 422/68, 69, 70; 436/150, 161, 175, 176, 177, 178; 73/61.1 C; 210/198.2, 321.1, 649, 656, 659

[56] References Cited

U.S. PATENT DOCUMENTS

| 4,403,039 | 9/1983 | Ban et al. ............ 422/70 X |
| 4,451,374 | 5/1984 | Peterson et al. ...... 422/70 X |
| 4,459,357 | 7/1984 | Jansen et al. ......... 422/70 X |

FOREIGN PATENT DOCUMENTS

| 0032770 | 7/1981 | European Pat. Off. .......... 422/70 |
| 0103663 | 6/1983 | Japan . | |
| 0165054 | 9/1983 | Japan ............................ 422/70 |
| 82/00773 | 3/1982 | PCT Int'l Appl. ............. 422/70 |
| 2115146 | 9/1983 | United Kingdom ........... 436/161 |

OTHER PUBLICATIONS

Heftmann, "Chromatography: A Laboratory Handbook of Chromatographic and Electrophoretic Methods", Third Edition, Van Nostrand Reinhold Co., New York, p. 318, 1975.

*Primary Examiner*—Barry S. Richman
*Assistant Examiner*—Robert J. Hill, Jr.
*Attorney, Agent, or Firm*—Sughrue, Mion, Zinn, Macpeak, and Seas

[57] ABSTRACT

In chromatographic analysis by the steps of adding a sample solution to a flow of an eluant, passing the eluant flow through a separation column thereby converting the eluant flow into an eluate flow containing component ions of the eluant flow in separate zones, passing the eluate flow through an ion-exchange membrane tube thereby allowing the eluate to come into contact with an aqueous solution of an $H^+$ form or $OH^-$ form electrolyte outside the tube through the wall of the membrane tube, substituting those of the component ions contained in the eluate flow which have the same type of electric charge as $H^+$ or $OH^-$ with said $H^+$ or $OH^-$ thereby giving rise to a deionized solution flow, and passing the deionized solution flow through a detection cell thereby causing the component ions which have survived the substitution to be detected as separated into distinct zones, improvements are obtained by causing the aqueous solutions of $H^+$ or $OH^-$ form electrolyte to be contacted with an insoluble ion exchanger of the same $H^+$ or $OH^-$ type as said electrolyte to the aqueous solution. Use of a high molecular weight electrolyte having a molecular weight of 500 or more permits detecting anion or cation present in a very low concentration with ample sensitivity and high reproducibility without provision of forwarding means.

7 Claims, 13 Drawing Figures

APPARATUS FOR CHROMATOGRAPHIC ANALYSIS

This is a division of application Ser. No. 656,212, filed Oct. 1, 1984.

FIELD OF THE INVENTION

This invention relates to a method for the chromatographic analysis of an aqueous solution for component ion species and to an apparatus to be used in working the method.

BACKGROUND OF THE INVENTION

In the removal of ion species or in the ion-exchange chromatography, ion species ionized to a high degree can be separated by the technique of ion-exchange resin and can be quantitatively analyzed by the use of an electroconductive cell, for example.

The first system of this kind was developed by Wickbold in *A. Anal. Chem.*, 132, 401 (1951). The initial apparatus so offered made use of no liquid pump and suffered from a disadvantage that the efficiency of the packed column was low and even the sensitivity was low. The ion chromatography subsequently developed by Small, Stevens, and Bauman (*Anal. Chem.*, 47, 1801 (1975)) incorporated the principle of high-speed liquid chromatography and particularly materialized high-sensitivity analysis for various ions by the use of a deionization column. In this apparatus, since ions persist in large amounts in the deionization column as adsorbed on the ion exchanger, the deionization column must be subjected to a treatment for the regeneration of ion exchanger with the flow path thereof switched to some other flow path during the treatment. This apparatus, therefore, necessitates provision of a separate liquid pump. As the result, the apparatus has a disadvantage that the construction thereof gains in complexity and the comsumption of acid or alkali regenerant is large. The method which uses ion-exchange membrane tubes in the place of the deionization column and effects analysis for anions by passing the eluate flow from the separation column through the afore-mentioned tubes, and causing cations in the eluate flow to depart outside from the ion-exchange membrane tubes through the membrane walls thereof by passing a reagent such as sulfuric acid or dodecylbenzenesulfonic acid through annular spaces formed between the outer wall surfaces of the ion-exchange membrane tubes and the inner wall surfaces of larger outer tubes disposed severally around the ion-exchange membrane tubes has been disclosed in Japanese Patent Application (OPI) Nos. 135156/81 and 57464/83, etc. (The term "OPI" as used herein means a "published unexamined Japanese patent application".) This method, however, is fated to the drawback that the reagent such as sulfuric acid or dodecylbenzenesulfonic acid by nature leaks inside into the ion-exchange membrane tubes through their membrane walls. This method, therefore, finds it improper to use this reagent in a high concentration. To cope with this trouble, this method inevitably necessitates means capable of regularly forwarding the reagent in a low concentration such as, for example, a pump and attendant piping and, at the same time, entails heavy consumption of acid for regeneration. An apparatus for working the method of this description becomes large and complicate.

Although various methods and apparatuses have been proposed to date for the analysis of aqueous solutions for component ions in minute amounts therein, none of them has proved satisfactory. The desirability of perfecting convenient and efficient method and apparatus for chromatographic analysis has been finding growing recoginition.

The inventors continued a diligent study for the purpose of making improvements capable of eliminating the numerous drawbacks mentioned above. They have consequently perfected a method for chromatographic analysis and an apparatus therefor which permit simultaneous, quick separation and detection of a plurality of component ions existing in minute amounts in an aqueous solution with high sensitivity and reproducibility over a protracted period of test.

SUMMARY OF THE INVENTION

This invention resides essentially in a method for the chromatographic analysis by the steps of adding sample solution to a flow of an eluant, passing the eluant flow through a separation column thereby converting the eluant flow into an eluate flow containing component ions of the eluant flow in separate zones, passing the eluate flow through an ion-exchange membrane tube thereby allowing the eluate to come into contact with an aqueous solution of an $H^+$ form or $OH^-$ form electrolyte outside the tube through the walls of the membrane tube, substituting those of the component ions contained in the eluate flow which have the same type of electric charge as $H^+$ or $OH^-$ with said $H^+$ or $OH^-$ thereby giving rise to a deionized solution flow, and passing the deionized solution flow through a detection cell thereby causing the component ions which have survived the substitution to be detected as separated into distinct zones, which method is characterized by the fact that the aqueous solution of $H^+$ or $OH^-$ form electrolyte has been contacted with an insoluble ion exchanger of the same $H^+$ or $OH^-$ type as said electrolyte and in an apparatus for the chromatographic analysis for ions comprising an eluant reservoir, a liquid pump, a sample inlet, a separation column disposed in a constant temperature bath, and a detection cell also disposed therein, arranged as serially connected in the order mentioned along the path through which the eluant flows, which apparatus is characterized by the fact that a deionizing device, obtained by placing an ion-exchange membrane tube for passing the eluant and an insoluble ion exchanger together in one container or separately in a composite container having the member containers interconnected with a liquid circulation path and filling voids in the container with an aqueous solution of $H^+$ or $OH^-$ form electrolyte selected to be the same $H^+$ or $OH^-$ type as the insoluble ion exchanger, is disposed within the constant temperature bath and the deionization device is inserted between the separation column and the detection cell as joined thereto.

The other objects and characteristic features of the present invention will become apparent to those skilled in the art as the disclosure is further made in the following description of a preferred embodiment of the invention, as illustrated in the accompanying drawings.

DESCRIPTION OF PREFERRED EMBODIMENTS

Figure 1:
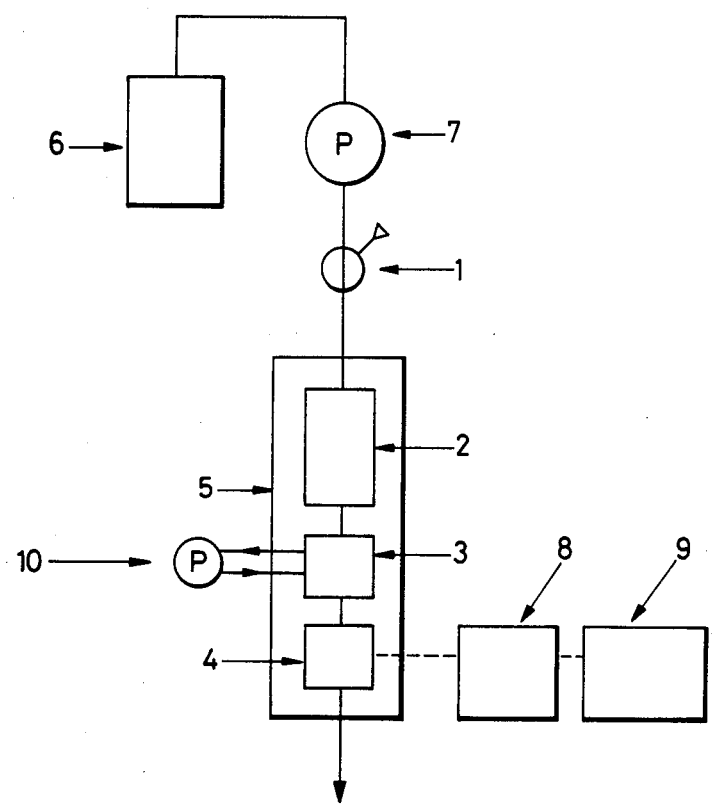
FIG. 1 is a flow diagram of a chromatographic analyzer to be used for working out a method and apparatus for deionization according to the present invention.

Now, this invention will be described in detail below. FIG. 1 is a flow diagram of a chromatographic analyzer of this invention and FIGS. 2a–2e are diagrams representing artist's concept of working examples of the deionizing device constituting an essential part of this invention. When reference to FIG. 1, from an eluant reservoir 6 the eluant is forwarded by a liquid pump 7 to a sample inlet 1. The eluant flow, mixed with a fixed amount of a sample at the sample inlet 1, is fed into a separation column 2 disposed inside a constant temperature bath 5. While the eluant flow containing the sample is passing through the separation column 2, the component ions in the sample are separated and concentrated as they undergo exchange of ion and adsorptive and desorptive actions caused by the packing. They are further eluted by the eluant to give rise to an eluate flow containing the component ions in separate zones. Then, the eluate flow is forwarded to a deionizing device 3 and passed through an ion-exchange membrane tube 12 held in a container 11 and formed in the shape of a coil (FIGS. 2a–2b), a basket (FIG. 2c), or plate (FIG. 2d) so that the eluate is allowed to come into contact with an aqueous solution of a $H^+$ form or $OH^-$ form electrolyte outside the tube through the wall of the membrane tube and those of the component ions contained in the eluate flow which have the same type of electric charge as the afore-mentioned $H^+$ or $OH^-$ are consequently substituted with the $H^+$ or $OH^-$. In other words, when the eluate flow in a cation-exchange membrane tube is allowed to come into contact with an aqueous solution of $H^+$ form electrolyte such as, for example, sulfuric acid through the medium of the tube, those of the component ions contained in the eluate flow which have the same electric charge as the $H^+$, namely cations such as, for example, $Na^+$ are substituted with the $H^+$. In the aqueous $Na_2CO_3$ solution generally used as an eluant, the $Na^+$ content is descreased because this cation is substituted with $H^+$, the corresponding anion $CO_3^{--}$ content forms an acid because the anion is combined with $H^+$, and $H_2CO_3$ which is a weak electrolyte is sparingly ionized, with the result that the overall ion concentration of the solution is notably lowered. In this manner, the eluate flow is deionized. When the resultant deionized solution flow is passed through a detection cell 4, the base line of the chromatogram is lowered. Consequently, the component ions which have survived the substitution are passed in separate zones through the detection cell and detected. The chromatograms which are displayed on a detector 8 and a recording meter 9 faithfully represent the component ions contained in minute amounts with high sensitivity.

In the meantime, an aqueous electrolyte solution 13 has its $H^+$ or $OH^-$ substituted with the ion migrating from the eluate flow. For example, sulfuric acid has its $H^+$ substituted with the cation $Na^+$ which has substituted $H^+$, with the result that the concentration of $H^+$ or $OH^-$ is lowered and, at the same time, the concentration of migrating ion is increased. Thus, the capacity for substitution dwindles. In the preceding case, the ion-exchange proceeds with the reaction of $2Na^+ + H_2SO_4 \rightarrow 2H^+ + Na_2SO_4$, thus the conversion of the aqueous sulfuric acid solution to an aqueous sodium sulfate solution proceeds. In the system, $H^+$ decreases and $Na^+$ builds up. The conventional method, at this point, discards the electrolyte solution. In contrast, in the method of this invention, since the aqueous electrolyte solution 13 has been contacted with an insoluble ion exchanger 14 of the same $H^+$ or $OH^-$ type as said electrolyte, the migrating ion gains in concentration and, at the same time, the ion exchanger occludes the migrating ion and the $H^+$ or $OH^-$ having the same type of electric charge as the migrating ion is released. Thus, the capacity for substitution is restored. $Na^+$ which is a migrating ion, for example, converts temporarily into $Na_2SO_4$ in sulfuric acid. Owing to the action of diffusion in the stationary phase or the action of diffusion in the mobile phase subjected to the action of agitation and fluid-flow, however, $Na^+$ is enabled to reach the cation exchanger and is sequestered therein. Thus, accumulation of $Na_2SO_4$ does not actually occur in sulfuric acid. The sulfuric acid, therefore, retains acidity, i.e., the concentration of $H^+$, always at a fixed level and consequently is capable of retaining the cation-exchange capacity at a high level approximating the initial level. Of course, the afore-mentioned action of restoraton is lowered and the $H^+$ or $OH^-$ concentration of the afore-mentioned aqueous electrolyte solution 13 is proportionately lowered eventually when the exchange capacity of the afore-mentioned ion exchanger 14 is exhausted. At this point, the use of the deionizing device is stopped as unserviceable. Thus, one serviceable term of the deionizing device expires. Naturally this term solely hinges on the exchange capacity of the ion exchanger. For this reason, the present invention discriminates the aforementioned insoluble ion exchanger by the magnitude of exchange capacity. Specifically, this invention specifies that the insoluble ion exchanger should possess exchange capacity of not less than 0.3 meq/ml. This specification is aimed at ensuring retention of service life and capacity efficiency of the deionizing device.

The second characteristic feature of this invention is conspicuous when the afore-mentioned aqueous electrolyte solution is an aqueous solution obtained by dissolving a high molecular weight electrolyte having a molecular weight of not less than 500 in water in a concentration of not less than 0.01N. As already described, the eluate flow is brought into contact with the aqueous electrolyte solution through the wall of the ion-exchange membrane tube and the component ion in the eluate flow is substituted with the $H^+$ or $H^-$ of the same type of electric charge. This process relies on the action of diffusion exerted to the ion which passes through the membrane wall. The intensity of this invention, therefore, depends on the difference between the ion concentrations in the solutions bordering on the opposite surfaces of the membrane wall. When the concentration of the aqueous electrolyte solution such as, for example, the concentration of $H^+$, is heightened and the concentration of the ion migrated into the aqueous solution is retained at as low a level as possible, the afore-mentioned action of diffusion is strengthened and, as the result, the substitution of H+ or OH− proceeds quickly. As already pointed out, since the conventional technique uses an aqueous low molecular weight electrolyte solution, both the cation and the anion of the electrolyte tend to diffuse through the membrane wall of the afore-mentioned ion-exchange membrane tube. The use of the electrolyte in a high concentration, therefore, must be avoided because such use constitutes a factor detrimental to the deionization. As the result, the conventional technique is compelled to incorporate an extra process aimed at retention of capacity for substitution. This invention elminates the problem of leakage of electrolyte by using a high molecular weight electrolyte as described above and, as the result, permits an addition to the electrolyte concentration. Owing to the high concentration of the electrolyte coupled with the action of sequestration and removal of migrating ion manifested by the afore-mentioned insoluble ion exchanger, the substituting ability of the aqueous electrolyte solution is retained at an extremely high level and, as the result, the length of the ion-exchange membrane tube can be decreased. Where the conventional technique necessitates use of an ion-exchange membrane tube having a diameter of 0.6 mm in length of 5 m, the method of this invention requires the use of the same tube in a much smaller length of 2 m. In this case, the concentration of the aqueous electrolyte solution is 0.05N as in the working examples described afterward. Further, since the action of diffusion gains in intensity in proportion as the concentration is heightened, the aqueous electrolyte solution is not always required to be fluid-flowed and agitated. For the method of this invention, therefore, it suffices to use a stationary type deionizing device, i.e., to use the aqueous electrolyte solution 13 without being fluid-flowed and agitated with a pump 10 or a stirrer 15.

Figure 2A:
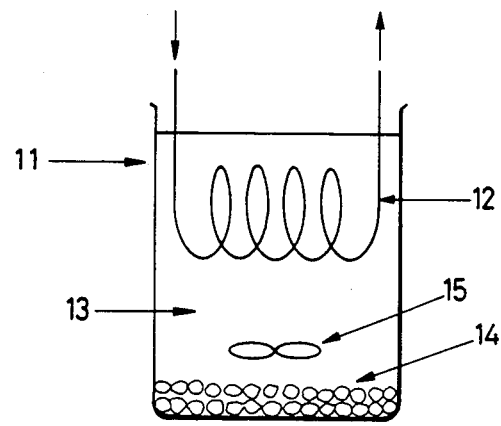
FIGS. 2a–2e are diagrams represents artist's concept of working examples of the deionizing device.
Figure 2B:
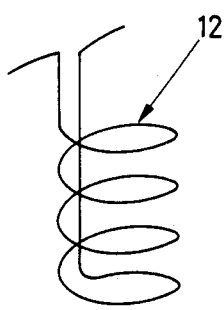
Figure 2C:
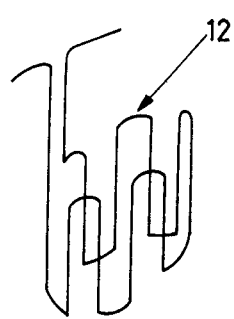
Figure 2D:
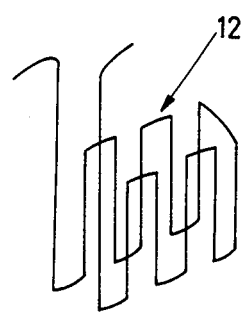
Figure 2E:
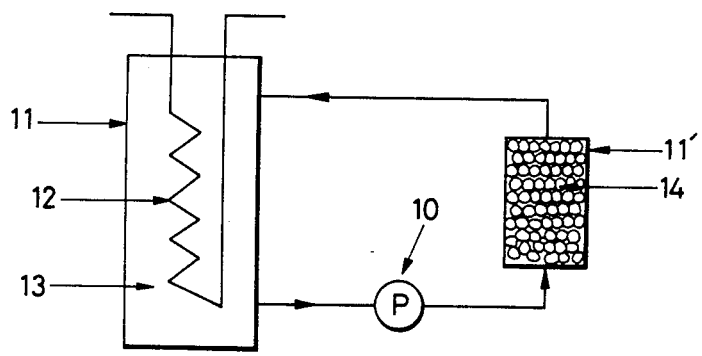

In that case, since the inclination of the diffusion to rely solely on molecular diffusion becomes increasingly conspicuous, it proves advantageous to shorten the distance over which the ion is migrated by diffusion. On the part of the deionizing device 3, this decrease of the distance of diffusion can be obtained by forming the ion-exchange membrane tube in the shape of a coil, a basket, or a plate as illustrated in FIGS. 2b–2d, placing insoluble ion-exchange beads in a manner enclosing the tube as packed closely thereto, placing the tube and the beads in one continer, and filling voids within the container, particularly between the tube and the beads and between the adjacent beads with the aqueous electrolyte solution. Though stationary in type, the deionizing device 3 so constructed can fully manifest the substituting ability. In contrast, the fluid-flow type deionizing devices such as the device having a stirrer 15 additionally incorporated in the container 11 as illustrated in FIG. 2a, the device adapted to expose the contents of the container to ultrasonic waves from an external source, and the device having the ion-exchange membrane tube accommodated in one container 11, placing insoluble ion-exchange beads 14 in the other container 11′ connected to the afore-mentioned container 11 with a liquid circulation path incorporating a circulation pump 10, and filling the containers 11, 11′ and the liquid circulation path with the aqueous electrolyte solution are allowed to agitate and fluid-flow the aqueous electrolyte solution with the stirrer, the ultrasonic waves, or the pump and therefore, are relieved of the restriction as to the distance between the tube and the ion-exchange beads. Where the size of the equipment raises no problem, the deionizing device can be easily adapted to use the ion exchanger in a large amount and, therefore, enjoys a long service life. The device of the type using separate containers for dissimilar functions as illustrated in FIG. 2e proves convenient when the ion exchanger is replaced or renewed.

Now, further details of the invention will be described.

The ion-exchange membrane to be used in the afore-mentioned deionizing device is typically produced by sulfonation (cation-exchange membrane) or amination (anion-exchange membrane) of a varying synthetic polymer such as, for example, polyethylene. Particularly useful examples of the ion-exchange membrane are sulfonated polyfluorocarbon membrane (marketed under trademark designation of "Nafion") which excels in resistance to solvents and which proves desirable because it is available in any desired size and an aminated polyfluorocarbon membrane disclosed in Japanese Patent Application (OPI) No. 111864/83.

The ion-exchange membrane tube 12 is required to be so constructed that the eluate flow emanating from the separation column will be led therethrough to the detector cell without causing any disturbance in the separate zones of the eluted components. Generally, it is desired to be an ion-exchange tube having a circular cross section and measuring 0.1 to 1 mm in inside diameter and 100 to 300 cm in length. If the inside diameter is more than 1 mm, the tube causes disturbance in the eluate flow. If it is less than 0.1 mm, the tube offers heavy resistance to the eluate flow.

The electrolyte to be used in the afore-mentioned deionizing device is a reagent which is capable of efficiently removing either cation or anion from the eluted components and the eluant through the ion-exchange membrane. Generally, this electrolyte is used in the form of an aqueous electrolyte solution of the acid form (H+ form) or the basic form (OH− form) of high degree of ionization.

Examples of the acid form electrolyte are low molecular weight electrolytes including inorganic acids such as nitric acid, sulfuric acid, and perchloric acid and anionic surfactants such as alkylbenzenesulfonic acid, alkyl sulfates, alkylnaphthalenesulfonic acid, dialkyl sulfosuccinates, and polyoxyethylene alkyl sulfates which have 1 to 16 carbon atoms in their alkyl groups and high molecular weight electrolytes including polystyrenesulfonic acid, polyvinylsulfonic acid, polyacrylsulfonic acid, ligninsulfonic acid naphthalenesulfonic acid-formalin condensate, polyacrylic acid, polymethacrylic acid, polyphosphoric acid, alginic acid, mucopolysaccharide, carboxymethyl cellulose, cellulose sulfate, starch sulfate, and carboxymethyl starch which have molecular weight exceeding 500.

Examples of the basic form electrolyte are low molecular weight electrolytes including hydroxides of alkali metals and alkaline earth metals and cationic surfactants such as alkyl amine salts and quaternary ammonium salts having 0 to 16 carbon atoms in their alkyl groups and high molecular weight electrolytes including glycol chitosan-methyl glycol chitosan, polyethylene imine, polyvinyl pyridinium, amino starch, and amino cellulose having molecular weight exceeding 500.

Any electrolyte, acid or basic form, having a molecular weight of less than 500 is not desirable because this electrolyte leaks inside into the ion-exchange membrane tube through the membrane wall. Any electrolyte having a molecular weight exceeding 1,000,000 is not desirable because this electrolyte acquires viscosity so high as to lower the speed of ion diffusion excessively. It is, therefore, especially desirable for the electrolyte used in this invention to possess a molecular weight in the range of 500 to 1,000,000. The high molecular weight electrolyte satisfying this requirement is characterized by the fact that the electrolyte, when used in a high concentration, is capable of detecting anion or cation present in a very low concentration with ample sensitivity and high reproducibility without necessitating adoption of forwarding means such as a pump heretofore used for supply of reagent in a fixed amount.

The insoluble ion exchanger which coexists with the electrolyte of the afore-mentioned deionizing device is capable of converting the electrolyte effected for deionization through the medium of the ion-exchange membrane into the original acid or basic form, and is used for the purpose of retaining the electrolyte falling near the ion-exchange membrane in a fresh condition.

The insoluble ion exchanger is disposed so as to be efficiently exposed to the electrolyte and permit deionization of either the cation or the anion of the electrolyte. It is desired to have a high exchange capacity per unit volume, i.e., at least 0.5 meq/ml. Examples of the insoluble ion exchanger satisfying the requirement are ion-exchange resin, ion-exchange membrane, and ion-exchange fibers which are commercially available.

Insoluble ion exchangers are readily available. Among other insoluble ion exchangers, acidic form cation-exchange resin products marketed under such trademark designations as Diaion SK1B (cross-linked polystyrene containing $SO_3H$ made by Mitsubishi Chemical), Amberlite IR-120 (cross-linked polystyrene containing $SO_3H$ made by Japan Organo), Dowex 50W (cross-linked polystyrene containing $SO_3H$ made by The Dow Chemical), Bio-Rad AG 50W (cross-linked polystyrene containing $SO_3H$ made by Bio-Rad AG), Muromac AG 50W (cross-linked polystyrene containing $SO_3H$ made by Muromachi Chemical), Amberlite 252 (cross-linked polystyrene containing $SO_3H$ made by Japan Organo), and Bio-Rad AGMP-50 (cross-linked polystyrene containing $SO_3H$ made by Bio-Rad AG), basic form anion-exchange resin products marketed under such trademark designations as Amberlite IRA-400 (polystyrene containing $—CH_2NMe_3Cl$ or $—CH_2N(CH_2CH_2OH)Me_2Cl$ made by Japan Organo) and Diaion PK208 (made by Mitsubishi Chemical), and insoluble crown ethers highly capable of retaining alkali metal ions marketed under trademark designations Kryptofix 22B and Kryotofix 221B (made by Merck) are particularly desirable.

In accordance with this invention, the decationizing device is composed of a cation-exchange membrane, an acid form aqueous electrolyte solution, and an acid form insoluble cation exchanger and the deanionizing device is composed of an anion-exchanger membrane, a basic form aqueous electrolyte solution, and a basic form insoluble anion exchanger.

The deionizing device may be of the stationary type involving neither fluid-flowing nor agitation. By incorporation of a device for agitation, circulation, electrophoresis, or ultrasonic wave, the deionizing device is enabled to provide ion exchange at an increased velocity. Since the ion-exchange capacity of the insoluble ion exchanger per unit volume is more than 50 times that of a solution type ion exchanger of a concentration of 0.01N, for example, the insoluble ion exchanger provides desired deionizing effect for a long time at a small application ratio. Periodically, the insoluble ion exchanger is replaced with a new supply because of loss of the deionizing ability. At the time of this replacement, the electrolyte is not always required to be replaced with a new supply.

As described in detail above, the present invention contemplates installing a deionizing device composed of an electrolyte and an insoluble ion exchanger outside an ion-exchange membrane tube for the purpose of efficient removal of either cation or anion from the eluted components and the eluant flow. Thus, the apparatus of this invention is not required to be complicated by the incorporation of a large stationary tank for storage of a low molecular weight electrolyte or of a device constantly operated with a liquid pump.

Further, since the deionizing device is small and light, it can be disposed within a small constant temperature bath. Since this device obtains the base line stably in spite of the use of measuring instruments sensitive to temperature such as, for example, a differential refractometer and an electroconductivity detector, the apparatus of this invention yields results of analysis with high sensitivity and reproducibility.

Now, the present invention will be described more specifically below with reference to working examples and comparative examples.

EXAMPLE 1

In a general-purpose liquid chromatograph (made by Toyo Soda and marketed under trademark designation of HLC-803B), a column of Teflon (polytetrafluoroethylene) measuring 5 cm in length and 4.6 mm in inside diameter and packed with an anion exchanger (cross-linked polystyrene containing $—SO_3H$ produced by Toyo Soda and marketed under trademark designation of TSK gel IC-Anion-PW) was set in place. As a deionizing device, an ion-exchange tube (sulfonated polyfluorocarbon membrane produced by Du Pont and marketed under trademark designation of Nafion) 2 m in length and 0.6 mm in inside diameter was wound in the shape of a coil. Then, by incorporation of a conductivity detector (produced by Toyo Soda and marketed under trademark designation of CM-8), an apparatus for chromatographic analysis was completed. The flow diagram of this apparatus is shown in FIG. 3.

Figure 3:
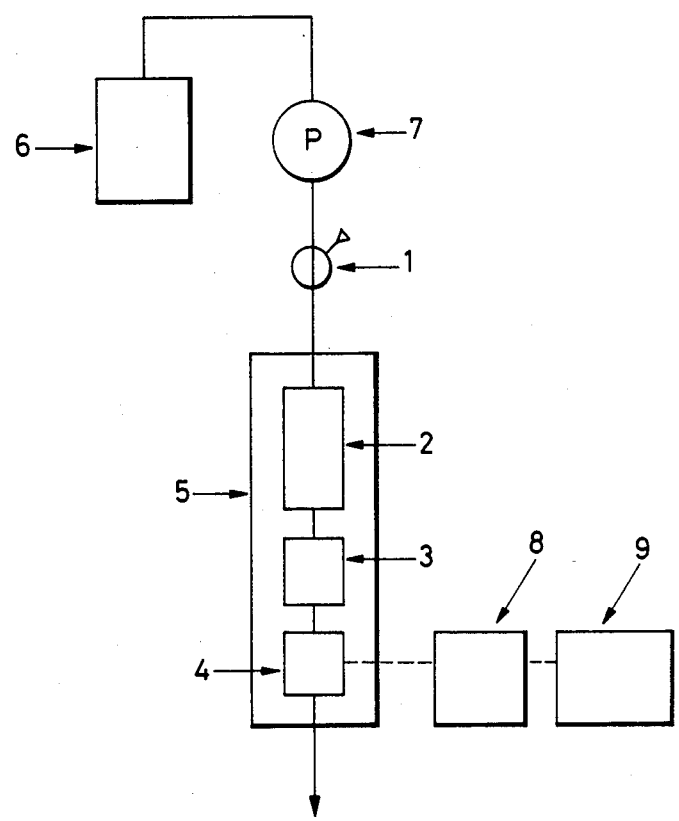
FIG. 3 is a flow diagram of a chromatographic analyzer used in comparative test of the effects of electrolyte in Example 1.

FIG. 3 depicts the apparatus for chromatographic analysis which essentially comprises a sample inlet valve 1, a constant temperature bath 5 incorporating therein a separation column 2 for separating a sample from the sample inlet valve 1, a deionizing device 2, and a detection cell 4 for detecting eluted component, and a liquid pump 7 for feeding the eluant from an eluant storage tank 6 to the afore-mentioned separation column 2. This apparatus for chromatographic analysis was provided with a detector 8 and a recorder 9 which are usually provided for any apparatus of this class.

The deionizing device used herein was a stationary column prepared by filling a glass beaker of inner volume of 100 ml with an aqueous high molecular weight electrolyte solution of a concentration of 0.05N. It was adapted to measure the change of conductivity along the course of time.

All the acid form high molecular weight electrolytes having molecular weights in the range of 500 to 1,000,000 were found to show conductivity at low levels of not more than 24 $\mu s/cm$ as shown in Table 1. As the eluant, an aqueous solution containing 2 mM NaHCO$_3$ and 1.6 mM Na$_2$CO$_3$ was fed at a flow volume of 1.0 ml/min. When the deionizing device was put out of use, the conductivity rose to a high level of 600 μs/cm.

Figure 4:
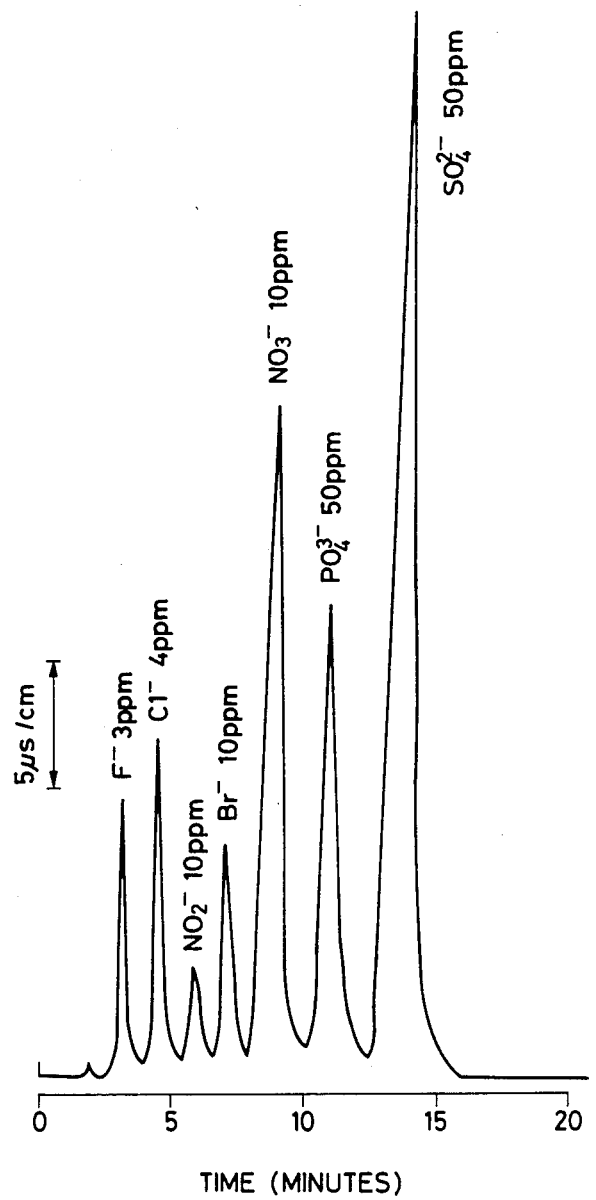
FIG. 4 is a chromatogram of seven anion species passed through a separation column and a deionizing device and detected by a conductivity detector by the procedure of Example 1. p

FIG. 4 shows a chromatogram of 7 standard anions obtained when polystyrenesulfonic acid having a molecular weight of 10,000 was used in a concentration of 0.05N as a high molecular electrolyte. The peak heights of the ions appearing on the chromatogram of FIG. 4 showed only slight variations within ±5% after elapse of 8 hours.

TABLE I
Deionizing Effect of High Molecular Weight Electrolyte

| High Molecular Weight Electrolyte | Molecular Weight | Conductivity (μs/cm) |
|---|---|---|
| Polystyrenesulfonic Acid | 800–1,000 | 22.4 |
| Polystyrenesulfonic Acid | 8,000–12,000 | 21.3 |
| Polystyrenesulfonic Acid | 40,000–60,000 | 20.5 |
| Polystyrenesulfonic Acid | 90,000–110,000 | 20.4 |
| Polyvinylsulfonic Acid | 100,000–140,000 | 21.5 |
| Polyacrylic Acid | 4,000–7,000 | 20.3 |

COMPARATIVE EXAMPLE 1

The procedure of Example 1 was repeated, except that low molecular weight electrolytes such as nitric acid, sulfuric acid, and dodecylbenzenesulfonic acid which have molecular weights not exceeding 500 were used in place of high molecular weight electrolytes.

The conductivity indicated was 220 μs/cm for nitric acid, 35 μs/cm for sulfuric acid, 23 μs/cm for dodecylbenzenesulfonic acid respectively. The data imply that the afore-mentioned anions leaked inside into the ion-exchange membrane tube.

Further, the peak heights appearing in the chromatogram gradually decreased with elapse of time. After elapse of 8 hours, the peak heights were less than 80% of the initial peak heights.

EXAMPLES 2–5 AND COMPARATIVE EXAMPLE 2

A deionizing device illustrated in FIG. 2a was obtained by using a cation-exchange membrane tube (produced by Du Pont and marketed under trademark designation of Nafion 811) 2 m in length and 0.6 mm in inside diameter as an ion-exchange membrane tube, 300 ml of an acid form aqueous electrolyte solution of a concentration of 0.05N as an aqueous electrolyte solution, and an acid form cation-exchange resin (2 meq/ml) (produced by Japan Organo and marketed under trademark designation of Amberlite IR-120) as an ion-exchange resin and immersing them in a beaker of Pyrex glass (350 ml in inner volume).

For measurement, an apparatus (produced by Toyo Soda and marketed under trademark designation of HLC-601) provided with a liquid pump, a sample inlet, a constant temperature bath, an electroconductivity detector, and a data processing unit was used. For chromatographic analysis, an aqueous solution containing 2 mM NaHCO$_3$ and 1.6 mM Na$_2$CO$_3$ was fed as an eluant at a flow volume of 1.2 ml/min to a separation column 5 cm in length and 4.6 mm in inside diameter (produced by Toyo Soda and marketed under trademark dsignation of TSK gel IC-Anion-PW) at a fixed temperature of 30° C.

To follow changes of peak heights in chromatogram, sodium salts of fluoride, chloride, nitrous acid, bromide, nitric acid, phosphoric acid, and sulfuric acid were prepared as standard specimens and used each in a sample size of 100 μl.

The afore-mentioned deionizing device was interposed between the separation column and the electroconductivity detector and operated to test various electrolytes for deionizing effect. The results are shown in Table II.

In Comparative Example 2, deionized water was used in place of an aqueous electrolyte solution and was agitated. The conductivity indicated increased with elapse of time. It reached 160 μs/cm after elapse of 1 hour, indicating a conspicuous decline of the deionizing ability. In this case, the analysis of standard specimen failed as noted from the chromatogram of FIG. 5a.

In Examples 2–5, no conspicuous change was observed in conductivity along the course of time. Thus, there was obtained a good chromatogram.

Figure 5C:
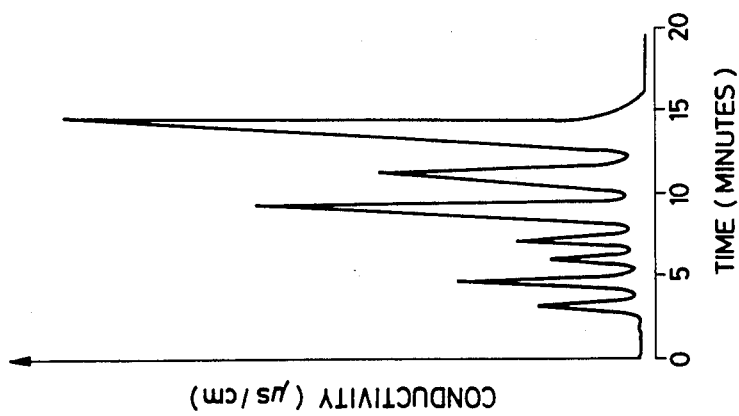
FIGS. 5a to 5c are a set of chromatograms for characterizing the results of the use of the method and appratus of this invention.
Figure 5B:
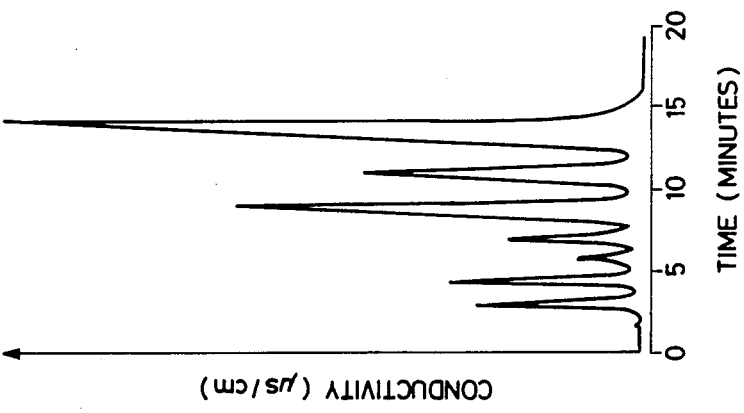
Figure 5A:
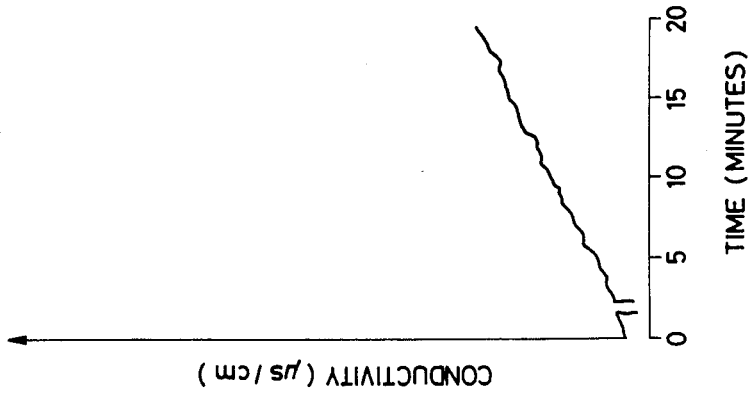

The chromatograms of Examples 3–4 are shown in FIGS. 5b and 5c.

It is noted from Table II that the values of conductivity obtained in Examples 2–3 are higher than those obtained in Examples 4–5. This is because such low molecular weight electrolytes as sulfuric acid and dodecylbenzenesulfonic acid constantly leaked inside into the membrane tubes. In contrast, polystyrenesulfonic acid is a high molecular weight electrolyte and, therefore, leaked inside sparingly into the membrane tube. This explains why the values of conductivity were low in Examples 4–5.

Comparison of the results of Examples 2–5 reveals that use of a high molecular weight electrolyte is particularly desirable because of a low molecular weight electrolyte keeps leaking inside into the membrane tube and the deionizing effect is gradually lowered during a protracted operation.

TABLE II

| | Electrolyte | Insoluble Ion Exchanger | Conductivity of Eluant (μs/cm) | | |
|---|---|---|---|---|---|
| | | | After 1 hours | After 5 hours | After 10 hours |
| Example 2 | H$_2$SO$_4$ | Amberlite IR-120 | 35 | 37 | 40 |
| Example 3 | Dodecylbenzenesulfonic acid | Same as above | 21 | 23 | 25 |
| Example 4 | Polystyrenesulfonic acid (molecular weight 1,000) | Same as above | 20 | 20 | 20 |
| Example 5 | Polystyrenesulfonic acid (molecular weight 10,000) | Same as above | 20 | 20 | 20 |
| Comparative Example 2 | Deionized water | Same as above | 40 | 160 | 600 |

EXAMPLES 6–8 AND COMPARATIVE EXAMPLE 3

These experiments were aimed at comparing operations using an insoluble ion exchanger and an operation not using any insoluble ion exchanger and demonstrating the usefulness of this invention for analysis involving a deionizing device in terms of both capacity and method.

The insoluble ion exchangers, Diaion SK1B (exchange capacity 2 meq/ml) made by Mitsubishi Chemical, Dowex 50W (2 meq/ml) made by the Dow Chemical, and TSK gel IEX-210 (1.5 meq/ml) made by Toyo soda, were washed with hydrochloric acid and washed with water and, consequently, changed to acid form. They were used each in a sample size of 10 ml.

A deionizing device had an inner volume of not more than 500 ml and an electrolyte solution of a concentration of 0.05N was used in an amount of 90% (450 ml) of inner volume of the device. As means of accelerating the deionization, the method of agitation by the use of a magnet stirrer made by Mitamura Rikensha, the method of circulation by the use of a peristaltic pump made by Art Kagaku, and the method of ultrasonic wave by the use of an ultrasonic wave generator made by Sharp were compared for the effect of diffusion.

The chromatographic apparatus and the conditions for chromatographic analysis were the same as those used in Examples 2–5 and Comparative Example 2. The data of deionizing effect thus obtained are shown in Table III.

Figure 6A:
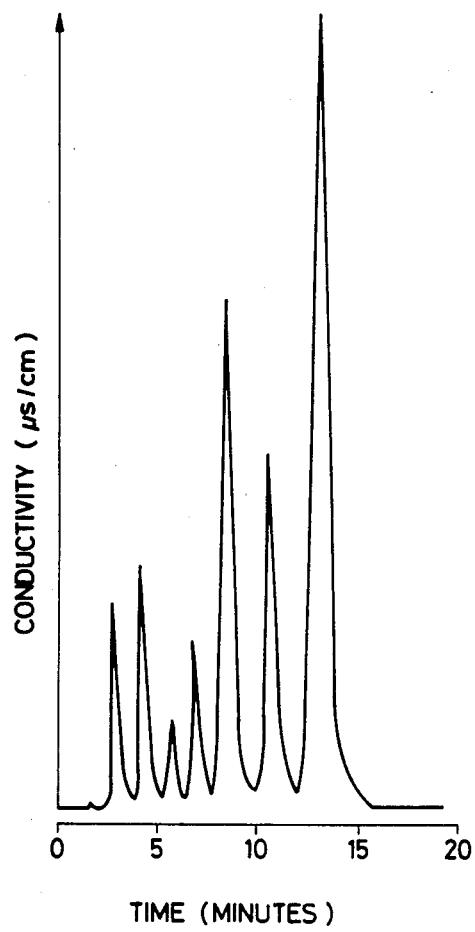
FIGS. 6a and 6b are a pair of chromatograms showing changes in peak height along the course of time obtained without using an insoluble ion exchanger.
Figure 6B:
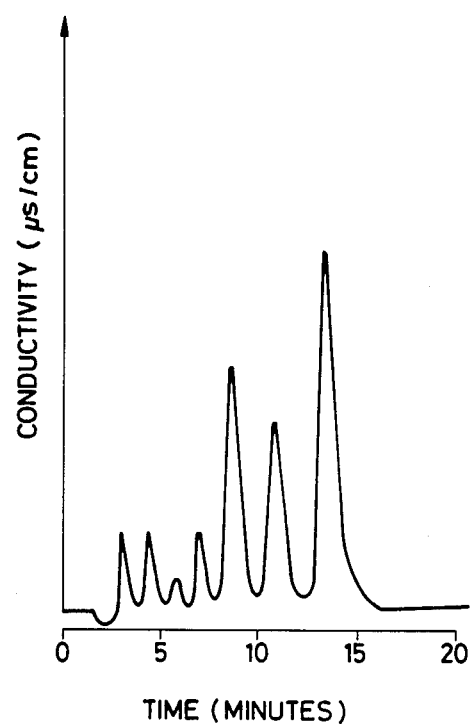

In Comparative Example 3 in which no insoluble ion exchaner was used, the conductivity increased with elapse of time. As indicated in FIGS. 6a and 6b, the peak heights after elapse of 24 hours (b) were each bout ½ of those found after elapse of 1 hour (a), indicating notable fall of sensitivity.

In Examples 6–8, no conspicuous change was observed in conductivity along the course of time. The chromatograms obtained herein were similar to those of FIG. 5c.

Examples 6–8 gave data which indicate that the effect of deionization can be retained long in the presence of a high molecular weight electrolyte and an insoluble ion exchanger and further that miniaturization of deionizing device can be attained by improving the effect of diffusion.

While the invention has been described in detail and with reference to specific embodiment thereof, it will be apparent to one skilled in the art that various changes and modifications can be made therein without departing from the spirit and scope thereof.

What is claimed is:

1. In an apparatus for chromatographic analysis of ions comprising an eluant reservoir, a liquid pump, a sample inlet, a separation column disposed in a constant temperature bath, and a detection cell also disposed therein arranged and serially connected in the order mentioned along a path through which an eluant flows, which apparatus includes as an improvement a deionizing device, comprising an ion-exchange membrane tube for passing eluant and an insoluble ion exchanger together in one container or separately in a composite container made up of member containers having the member containers interconnected with a liquid circulation path, with voids in said one container or composite container being filled with an aqueous solution of a form high molecular weight electrolyte comprising polystyrene sulfonic acid having a molecular weight of from 500 to 1,000,000, the high molecular weight of said electrolyte preventing leakage of said electrolyte through the membrane, the insoluble ion exchanger being an acid type ion exchanger and the aqueous solution being in contact with said insoluble ion exchanger which retains the aqueous solution in a fresh condition, wherein said deionization device is disposed between and connected to said separation column and said detection cell within said constant temperature bath.

2. An apparatus according to claim 1, wherein said deionizing device comprises one container containing said ion-exchange membrane tube in the shape of a coil, a basket, or a plate and said insoluble ion exchanger in the form of beads packed closely around said tube, with voids in said one container being filled with said aqueous solution of electrolyte.

3. An apparatus according to claim 1, wherein said deionizing device comprises one container containing said ion-exchange membrane tube in the shape of a coil, a basket, or a plate, said insoluble ion exchanger in the form of powder, and a stirrer, with voids in said one container being filled with said aqueous solution of electrolyte.

TABLE III

|  | Electrolyte | Insoluble Ion Exchanger | Deionizing Device | | Conductivity of Eluant (μs/cm) | | |
|---|---|---|---|---|---|---|---|
|  |  |  | Capacity | Type | After 1 hour | After 12 hours | After 24 hours |
| Example 6 | Polystyrene-sulfonic acid (molecular weight 1,000) | Dianion SK1B | 50 ml | Agitation | 20 | 20 | 20 |
| Example 7 | Polystyrene-sulfonic acid (molecular weight 10,000) | TSK gel IEX-210 | 50 ml | Circulation pump | 20 | 20 | 20 |
| Example 8 | Polystyrene-sulfonic acid (molecular weight 10,000) | Dowex 50W | 50 ml | Ultrasonic wave | 20 | 21 | 21 |
| Comparative Example 3 | Polystyrene-sulfonic acid (molecular weight 10,000) | None | 500 ml | Agitation | 20 | 32 | 44 |

4. The apparatus of claim 1 wherein the polystyrene sulfonic acid has a molecular weight of from 800 to 1,000,000.

5. An apparatus according to claim 1, wherein said deionizing device comprises a composite container made up of member containers, with one member container of said composite container containing said ion-exchange membrane tube formed in the shape of a coil, a basket, or a plate, and another member container of said composite container containing said insoluble ion-exchanger in the form of beads and being joined to said one member container with a liquid circulation path passing through a circulation pump, with voids in both member containers and said liquid circulation path being filled with said aqueous solution of electrolyte.

6. The apparatus of claim 5 wherein said polystyrene sulfonic acid has a concentration of 0.01N or more in said aqueous solution.

7. The apparatus according to claim 6 wherein said concentration of polystyrene sulfonic acid is at least 0.05N in said aqueous solution.

* * * * *